United States Patent [19]

Gitlitz

[11] 4,343,815
[45] Aug. 10, 1982

[54] METHOD FOR COMBATING FUNGI AND MITES USING CERTAIN TRIORGANOTIN COMPOUNDS

[75] Inventor: Melvin H. Gitlitz, Edison, N.J.

[73] Assignee: M&T Chemicals Inc., Woodbridge, N.J.

[21] Appl. No.: 881,248

[22] Filed: Feb. 27, 1978

Related U.S. Application Data

[63] Continuation of Ser. No. 392,960, Aug. 30, 1973, abandoned.

[51] Int. Cl.$^3$ ............................................. A01N 55/04
[52] U.S. Cl. ...................................... 424/288; 424/45; 424/357
[58] Field of Search ........................................ 424/288

[56] References Cited

U.S. PATENT DOCUMENTS

| | | | |
|---|---|---|---|
| 3,097,999 | 7/1963 | Koopmans | 424/288 |
| 3,305,442 | 2/1967 | Nishimoto et al. | 424/288 |
| 3,702,360 | 11/1972 | Graham | 424/288 |
| 3,745,219 | 7/1973 | Baum | 424/288 |

FOREIGN PATENT DOCUMENTS

| | | | |
|---|---|---|---|
| 797073 | 6/1958 | United Kingdom | 424/288 |
| 945068 | 12/1963 | United Kingdom | 424/288 |
| 1122371 | 8/1968 | United Kingdom | 424/288 |

*Primary Examiner*—Dale R. Ore
*Attorney, Agent, or Firm*—Stanley A. Marcus; Franklyn Schoenberg; Sheldon H. Parker

[57] ABSTRACT

Sterically-hindered triorganotin compounds of the general formula

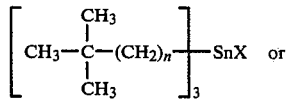 or

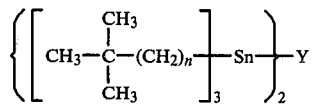

effectively combat fungi and mites when applied to objects, particularly plants, that are susceptible to attack by these organisms. The present compounds are particularly advantageous in that they are considerably less phytotoxic than homologous triorganotin compounds wherein the hydrocarbon radicals contain between 4 and 6 carbon atoms (e.g. n-butyl and n-hexyl radicals). In the foregoing formulae X is selected from the group consisting of a chlorine, bromine, fluorine, hydroxyl, cyanide, carbamate, thiocarbamate, amide ($NH_2$), amino ($NR_2^1$ or $NR^1H$), nitrate, enolate, carboxylate

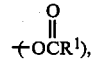

phenoxy, alkoxy (—$OR^1$) and mercaptide (—$SR^1$) radical wherein $R^1$ represents an alkyl or aryl radical containing between 1 and 12 carbon atoms, inclusive, Y is an oxygen, sulfur, or a sulfate radical and n is an integer between 0 and 4, inclusive.

1 Claim, No Drawings

METHOD FOR COMBATING FUNGI AND MITES USING CERTAIN TRIORGANOTIN COMPOUNDS

This is a continuation of application Ser. No. 392,960, filed Aug. 30, 1973, abandoned.

This invention relates to a method for selectively controlling fungi and mites using certain sterically-hindered triorganotin compounds. The organisms against which the compounds are effective are responsible for a considerable portion of the annual damage to agricultural crops. Many triorganotin compounds, particularly tri-n-butyltin and tri-n-amyltin derivatives effectively control fungi and mites. However, these organotin compounds are sufficiently non-selective toward desirable plant crops, in that while the organism attacking the plant is controlled, the plant itself is often killed or severely damaged.

SUMMARY OF THE INVENTION

It has now been found that sterically hindered triorganotin compounds of the general formula

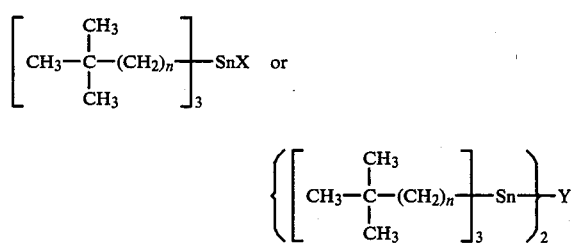

effectively control fungi and mites yet are relatively harmless toward plants to which efficacious amounts of these compounds are applied. In the foregoing formulae, X represents a radical selected from the group consisting of chlorine, bromine, fluorine, hydroxyl, cyanide, carbamate, thiocarbamate, amide ($NH_2$), amino(-$NR_2^1$ or $NR^1H$) nitrate, enolate, carboxylate

phenoxy, alkoxy (-$OR^1$), and mercaptide (-$SR^1$), wherein $R^1$ represents an alkyl or aryl radical containing between 1 and 12 carbon atoms, inclusive, Y is an oxygen, sulfur, or sulfate radical and n is an integer between 0 and 4, inclusive.

DETAILED DESCRIPTION OF THE INVENTION

The three hydrocarbon radicals of the present organotin compounds contain a tertiary carbon atom that is bonded to three methyl ($CH_3$-) radicals. The remaining valence of the tertiary carbon atom is satisfied by a bond to the tin atom or to an alkylene radical containing 1 to 4 carbon atoms which is in turn bonded to the tin atom. The preferred compounds can be conveniently classified as tri-t-butyl-, trineopentyl or tris(3,3-dimethylbutyl)tin derivatives.

Trineopentyltin and tri-t-butyltin halides wherein the halogen is chlorine, bromine or iodine are conveniently prepared by reacting at least three moles of the corresponding neopentyl- or t-butyl magnesium halide (the chloride, bromide or iodide) with stannic chloride, bromide or iodide. This is a well-known type of reaction and has been described in the chemical literature for the preparation of numerous other triorganotin derivatives.

Preferably a solution containing the alkyl-magnesium halide is added to a solution of the stannic halide. Suitable solvents for the stannic halide include aromatic hydrocarbons and halogenated hydrocarbons, although any compound which is a liquid at the reaction temperature and does not react with the stannic halide or the alkylmagnesium halide can be employed as solvents for the reaction. The alkylmagnesium halide is preferably dissolved in a linear or cyclic aliphatic ether containing between 4 and 10 carbon atoms. The temperature of the reaction mixture is maintained between ambient and 50° C. during addition of the alkylmagnesium halide to maximize the yield of the desired product.

Tris(3,3-dimethylbutyl)tin halide and the remaining organotin halide, wherein "n" of the foregoing formula is 2 to 4 can be prepared by reacting the corresponding alkylmagnesium halide with a stannic halide, however these compounds are preferably obtained by the reaction between a tris(3,3-dimethylalkyl) alkyl tin compound with the desired stannic halide. The alkyl radical is replaced by a halogen radical from the stannic chloride to yield the corresponding tris(3,3-dimethylalkyl)-tin halide.

The triorganotin halide obtained using either of the preceding reactions is a solid material at ambient temperature and can readily be converted to other derivatives such as the oxide, acetate, and sulfate using known reactions. The desired anionic radical can be introduced by reacting the corresponding halide or oxide with the reagent indicated in the following table.

| ORGANOTIN DERIVATIVE + | REAGENT | DESIRED PRODUCT |
|---|---|---|
| Chloride, Bromide or Iodide | Carboxylic acid + acid acceptor, e.g. pyridine | carboxylate, e.g. acetate |
| Chloride, Bromide or Iodide | alkali metal salt of a carboxylic acid | carboxylate, e.g. acetate |
| Chloride, Bromide or Iodide | aqueous solution of alkali metal hydroxide | oxide (or hydroxide) |
| Chloride, Bromide or Iodide | alkali metal alkoxide of alcohol + acid acceptor | alkoxide |
| Chloride, Bromide or Iodide | alkali metal phenoxide or phenol + acid acceptor | phenoxide |
| Chloride, Bromide or Iodide | potassium fluoride or hydrofluoric acid | fluoride |
| Chloride, Bromide or Iodide | alkali metal sulfide | sulfide |
| Chloride, Bromide or Iodide | alkali metal sulfate | sulfate |
| Chloride, Bromide or Iodide | mercaptan + acid acceptor | mercaptide |
| Oxide (or hydroxide) | carboxylic acid or anhydride | carboxylate |
| Oxide (or hydroxide) | alcohol (or phenol) | alkoxide (or phenoxide) |
| Oxide (or hydroxide) | hydrofluoric acid | fluoride |
| Oxide (or hydroxide) | dilute (10-25 weight %) aqueous sulfuric acid | sulfate |
| Oxide (or hydroxide) | hydrogen sulfide | sulfide |
| Oxide (or hydroxide) | alkyl or aryl mercaptan | mercaptide |

The reaction conditions such as preferred solvents, temperatures and reaction times for preparing the derivatives summarized in the preceding table are known in the art and, therefore, do not require a detailed description in the present specification. A comprehensive treatment of this subject matter together with voluminous literature references is contained in an article by R. K. Ingham et al. that appeared in the October, 1960 issue of CHEMICAL REVIEWS (p.p. 459-539). The resultant sterically-hindered triorganotin compounds may be either liquid or solid materials at ambient temperature, depending upon the type of substituents represented by X and Y.

The sterically-hindered triorganotin compounds effectively combat undesirable mites and fungi on plants to which the compounds are applied. A single application of these compounds can provide residual and extended control of many varieties of fungi and mites for a considerable period of time, the duration of which is dependent to some extent upon mechanical and biological influences, including weather, but is sometimes as long as several months.

In preparing compositions for application to plants the organotin compound is often augmented or modified by combining it with one or more commonly employed pesticide additives or adjuvants including organic solvents, water or other liquid carriers, surfactants to aid in dispersing or emulsifying the organotin compound or particulate and finely comminuted or divided solid carriers. Depending upon the concentration of the tin compound in these compositions, they can be employed either directly to control the organisms or as concentrates which are subsequently diluted with one or more additional inert carriers to produce the ultimate treating compositions. In compositions to be employed as concentrates, the present triorganotin compounds can be present as a concentration of from about 5 to about 98% by weight. Other biologically active agents that are chemically compatible with the present triorganotin compounds can also be added.

The optimum concentration of tin compounds to be employed as toxicant in a composition for application to the organism directly or by employing its habitat for food as carrier, may vary provided that the organism is contacted with an effective dose of the toxicant. The actual weight of compound constituting an effective dose is primarily dependent upon the susceptibility of a particular organism to the tin compound. For combating apple scab, good results are obtained with liquid or dust compositions containing as little as three parts per million by weight of toxicant. Compositions containing up to 90 percent by weight of toxicant can be employed in the treatment of a mite-infested environment.

In the preparation of dust compositions, the organotin compound can be blended with many commonly employed finely divided solids, such as fuller's earth, attapulgite, bentonite, pyrophyllite, vermiculite, diatomaceous earth, talc, chalk, gypsum, wood flour, and the like. In such operations, the finely divided carrier is ground or mixed with the toxicant or wetted with a dispersion of the toxicant in a volatile liquid. Depending upon the proportions of ingredients, these compositions can be employed as concentrates and subsequently diluted with additional solid of the types indicated hereinbefore, to obtain the desired amount of active ingredient in a comminuted composition adapted for the control of pests. Also, such concentrate dust compositions can be incorporated in intimate admixture with anionic, cationic or non-ionic surfactants which act as emulsifying or dispersing agents to form spray concentrates. Such concentrates are readily dispersible in liquid carriers to form spray compositions or liquid formulations containing the toxicants in any desired amount. The choice of surface active agent and amount thereof employed are determined by the ability of the agent to facilitate the dispersing of the concentrate in the liquid carrier to produce the desired liquid composition. Suitable liquid carriers include water, methanol, ethanol, isopropanol, methyl ethyl ketone, acetone, methylene chloride, chlorobenzene, toluene, xylene, and petroleum distillates. Among the preferred petroleum distillates are those boiling almost entirely under 400° F. at atmospheric pressure and having a flash point above about 80° F.

Alternatively, one or more of the present triorganotin compounds can be dissolved in a suitable water-immiscible organic liquid and a surface active dispersing agent to produce emulsifiable concentrates which may be further diluted with water and oil to form spray mixtures in the form of oil-in-water emulsions. In such compositions, the carrier comprises an aqueous emulsion, i.e. a mixture of water-immiscible solvent, emulsifying agent and water. Preferred dispersing agents for these compositions are oil soluble and include the condensation products of alkylene oxides with phenols and organic and inorganic acids, polyoxyethylene derivatives of sorbitan esters, alkylarylsulfonates, complex ether alcohols, mahogany soaps and the like. Suitable organic liquids to be employed in the compositions include petroleum distillates, hexanol, liquid halohydrocarbons and synthetic organic oils. The surface active dispersing agents are usually employed in the liquid dispersions and aqueous emulsions in the amount of from about 1 to about 20 percent by weight of the combined weight of the dispersing agent and the active toxicant.

When operating in accordance with the present invention, the organotin compound or a composition containing the compound can be applied directly to the undesirable organism or to the site to be protected. Applications to the foliage of plants is conveniently carried out using power dusters, boom sprayers and spray dusters. When employed in this manner the compositions should not contain any significant amounts of phytotoxic diluents. In large scale operations, dusts or low volume sprays may be applied from an aircraft.

The following examples represent preferred embodiments of the present invention, and are not intended to limit the scope thereof. All parts and percentages are by weight unless otherwise specified.

EXAMPLES

EXAMPLE 1—Preparation of trineopentyltin chloride

To 12.1 g (0.5 g. atom) of magnesium turnings heated to a temperature of 30° C. under a nitrogen atmosphere was added a 25 c.c. portion of a solution containing 53.3 g. (0.5 mole) of 1-chloro-2,2-dimethylpropane dissolved in 200 c.c. of anhydrous diethyl ether. The reaction was initiated using a few drops of ethylene dibromide. The remaining portion of the 1-chloro-2,2-dimethylpropane solution was gradually added during a period of one hour while the reaction mixture was heated to the boiling point. Heating was continued for an additional six hours during which time 15 c.c. of a 3 normal solution of butylmagnesium chloride in diethyl ether was added to react with any impurities which could prevent or inhibit the formation of the neopentylmagnesium chloride. A small particle of iodine was also added as an initiator for the reaction. The reaction mixture was allowed to cool to ambient temperature and remain at this temperature for about 64 hours, during which time stirring of the mixture was continued. At the end of this period all of the magnesium appeared to have reacted. A 100 c.c. portion of diethyl ether was added to compensate for solvent loss resulting from evaporation, after which the reaction mixture was heated to the boiling point for two hours. A portion of this solution containing 0.167 mole of neopentylmagnesium chloride was added dropwise to a stirred solution of stannic chloride (34.8 g., 0.134 mole) dissolved in 300 c.c. benzene. The reaction was conducted under a nitrogen atmosphere and the temperature of the reaction mixture was maintained below 45° C. Following completion of the addition the reaction mixture was heated to the boiling point for two hours, then allowed to cool to ambient temperature. The resultant mixture was combined with a solution containing 100 g. ammonium chloride and 300 c.c. water while maintaining the temperatures of the mixtue below 30° C. The solid which precipated was removed, yielding a two-phase liquid. The organic portion of the liquid phase was freed from water by combining it with a portion of anhydrous magnesium sulfate, which was subsequently removed by filtration. The solvent was removed under reduced pressure to yield 45.1 g. (91.6% yield) of a white solid. A 43 g. portion of the solid was recrystallized by dissolving it in 200 c.c. of warm hexane and gradually cooling the resultant solution to −70° C. The recrystallized trineopentyltin chloride was colorless and melted between 110°–112° C. The melting range reported in the chemical literature is 109°–111° C.

Bis-trineopentyltin oxide was prepared by adding, over a 15 minute period, a solution containing 12.0 g. (0.3 mole) sodium hydroxide and 125 c.c. water to 73.5 g. (0.2 mole) of trineopentyltin chloride dissolved in 500 c.c. of acetone. The mixture was cooled using an ice-water mixture during the addition and for 30 minutes thereafter, whereupon 1 liter of water was added. The resultant oxide, a white solid, was recovered by filtration, washed using two liters of water and then dried. The oxide was obtained in 98.5% yield and melted between 210° and 214° C. The compound was found to contain 34.11% by weight of tin. The theoretical value for the oxide is 34.9%.

EXAMPLE 2—Preparation of tris(3,3-dimethylbutyl)tin chloride and the corresponding hydroxide.

A reaction vessel was charged with 12.16 g. (0.5 g.atom) of magnesium chips and 15 c.c. of a solution containing 60.3 g. (0.5 mole) 1-chloro-3,3-dimethylbutane dissolved in 200 c.c. of tetrahydrofuran. A nitrogen atmosphere was established within the vessel. The reaction was initiated by the addition of a few drops of ethylene dibromide, whereupon the remaining portion of the aforementioned tetrahydrofuran solution was added over a period of 1.5 hours. External heating was applied to maintain the reaction mixture at the boiling point. Heating was continued for 1 hour following completion of the addition, at which time the liquid phase was separated from the unreacted magnesium (0.32 g.) by decantation. A portion of this liquid phase containing 0.44 mole of 3,3-dimethylbutylmagnesium chloride was charged into a reaction vessel containing a nitrogen atmosphere. A solution of 31.2 g. (0.13 mole) of methyltin trichloride dissolved in 100 c.c. benzene was gradually added over 0.33 hours to the stirred contents of the reaction vessel. External cooling was applied as required to maintain the reaction mixture at 40° C. Following completion of the addition the resultant mixture was stirred for about 16 hours at ambient temperature, after which the contents of the reaction vessel were heated at the boiling point for 1 hour, then hydrolyzed using a solution of citric acid (50 g.) in 250 c.c. water. The organic phase was then separated, dried using a portion of anhydrous magnesium sulfate and the organic solvents removed under reduced pressure while the mixture was maintained at a temperature of about 40° C. The resultant colorless oil, obtained in 97% yield, was purified by combining a 35 g. portion of the oil with methanol, cooling the mixture to −20° C. and triturating the semi-solid mass. The white solid was isolated and recrystallized using a 60/40 volume ratio mixture of methanol/ethanol to yield methyl tris(3,3-dimethylbutyl)tin in 56% yield, based on starting materials.

Tris(3,3-dimethylbutyl)tin chloride was prepared by the gradual addition of stannic chloride (13.0 g., 0.05 mole) dissolved in 50 c.c. pentane to a solution containing 19.5 g. (0.05 mole) of methyl tris(3,3-dimethylbutyl)tin dissovled in 50 c.c. pentane. The addition required 20 minutes and was performed under a nitrogen atmosphere. External cooling was applied as necessary to maintain the temperature of the reaction mixture below 27° C. Following completion of the addition the resulant mixture was heated at the boiling point for 0.5 hour, then allowed to cool to ambient temperature. A solution containing 2 c.c. of 12 normal aqueous hydrochloric acid and 100 c.c. water was added to the reaction mixture over a three minute period, followed by 50 c.c. of benzene. The organic liquid phase was separated, combined with 102 c.c. of an aqueous hydrochloric acid solution as previously described, after which the organic solvent was separated, dried using a portion of anhydrous magnesium sulfate and the organic solvents removed under reduced pressure. A 10 g. portion of the resultant white solid residue, obtained in 90% yield, was recrystallized from 100 c.c. of hexane and exhibited the following analysis, by weight:

| tin | 28.88% | (28.97% theoretical) |
|---|---|---|
| chlorine | 8.60% | ( 8.65% theoretical) |

Tris(3,3-dimethylbutyl)tin hydroxide was prepared by adding, over a 15 minute period, a solution containing 6.0 g. (0.15 mole) of sodium hydroxide, 50 c.c. water and 50 c.c. methanol to 30.7 g. (0.075 mole) tris-3,3-dimethylbutyltin chloride dissolved in 300 c.c. methanol. The stirred reaction mixture was maintained at a temperature of 40° C. during the addition, following which it was heated to the boiling point (70° C.) for 0.5 hour. The mixture was then cooled to 10° C. and stirred for 0.5 hour. The white solid material in the reaction vessel was isolated by filtration, washed with 750 c.c. water containing 20 drops of an anionic surfactant, then with dionized water until the recovered liquid was free of chloride ion. The solid material was obtained in 96.5% yield and upon analysis was found to contain 30.45% by weight of tin. The theoretical tin content of tris(3,3-dimethylbutyl)tin hydroxide is 30.34%.

Bis(tri-t-butyltin)oxide was prepared as described by Kandil and Allred [Journal of the Chemical Society, A, 2987–92 (1970)]. The procedure as set forth in this article is reproduced below.

Unless otherwise stated, each reaction mixture was hydrolyzed with dilute hydrochloric acid. The organic layer was separated, the aqueous layer was extracted with diethyl ether, the combined solutions were dried anhydrous (MgSO$_4$) and filtered, and the solvent was removed by pumping.

Di-t-butyltin dichloride. The Grignard reagent from t-butyl chloride (92.5 g., 1 mole), magnesium (24.3 g., 1 mole) and tetrahydrofuran (1 l.) was added dropwise to a solution of tin(iv) chloride (104 g., 0.4 mole) in heptane (1 l.). A vigorous reaction started at once and magnesium chloride precipitated. After completion of the addition, the mixture was refluxed for 4 hrs. Cooling and work-up gave a yellow oil. This was distilled to give the desired product as a clear oil which solidified readily (70.0 g., 58%), m.p. 42°–43° (lit., 142°); b.p. 66°/3 mm.; n.m.4. 81.45(s).

Di-t-butyltin chloride fluoride. An ethereal solution of di-t-butyltin dichloride (10 g., 50 ml.) was shaken vigorously with a filtered solution of sodium fluoride (3 g.) in aqueous ethanol (50 ml.). The white solid formed at the interface, was filtered, and washed with 95% ethanol followed by ether (7.0 g., 74%); the solid turns light brown at 254° but does not melt. (Found: C, 33.4; H, 6.4; Cl, 9.2; F, 8.7; Sn, 43.3. C$_8$H$_{18}$ClFSn requires C, 33.45; H, 6.3; Cl, 12.25; F, 6.65; Sn, 41.3%.

Tri-t-butyltin chloride. A suspension of di-t-butyltin chloride fluoride (5.0 g., 0.017 mole) in heptane (100 ml.) was cooled to −78° C., and a pentane solution of t-butyl-lithium (20 ml., 1.95 M) was added dropwise. After the addition was completed, stirring was continued for 2 hrs., the cooling bath was removed, and the mixture was allowed to warm to room temperature with stirring for 6 more hrs. The resulting pale yellow mixture was worked up to give a thick, pale yellow oil which was chromatographed with pentane. Evaporation of the solvent left a clear oil which solidified spontaneously (5.0 g., 88.3%), m.p. 31–32; (b.p. 122°–123°/5 mm. (Found: C, 44.15; H, 8.15; Cl, 10.95. C$_{12}$H$_{27}$ClSn requires C, 44.3; H, 8.35; Cl, 10.9%); n.m.r. 61.35 (s).

Hexa-t-butyldistannoxane. An ethereal solution of the tri-t-butyltin chlorine was hydrolysed by shaking with an aqueous sodium hydroxide solution. The ether was boiled off to give a white crystalline solid. This can be sublimed at 265° (decomp.) under reduced pressure, m.p. 170° (from methanol-ether). (Found: C. 48.4; H, 9.3%; M, 583. C$_{24}$H$_{54}$OSn$_2$ requires C, 48.35; H, 9.15%; M, 596.1); n.m.r. 61.28(s).

BIOLOGICAL ACTIVITY OF STERICALLY-HINDERED TRIORGANOTIN COMPOUNDS

1. General Evaluation Method

Trineopentyltin chloride, the corresponding oxide, tris(3,3-dimethylbutyl)tin chloride, the corresponding hydroxide and bis(tri-t-butyltin)oxide were evaluated in the form of sprayable compositions prepared by dissolving or dispersing the compound in a 90/10 weight ratio water/acetone mixture containing a small amount of a non-ionic surfactant. The resultant composition was then diluted using a water-surfactant mixture to obtain the desired concentration of tin compound while maintaining the surfactant concentration at 100 parts per million (p.p.m.). Samples which proved difficult to emulsify were homogenized using a colloid mill or tissue homogenizer.

2. Evaluation of the Effectiveness of the Sterically-Hindered Triorganotin Compounds Against Specific Organisms The efficacy of representative triorganotin compounds of this invention as fungicides and miticides is summarized in the following section. The fungi employed were powdery bean mildew, (Erysiphe polygoni), apple mildew, apple scab, tomato early blight (Alternia solani), leaf spot of rice (helminthosporium). The mite employed was the two-spotted spider mite.

The rating system for determining control of the organisms was based on a numerical scale wherein a rating of 10 indicated 100% control (no surviving mites or fungus) and a rating of 0 indicated no control, i.e. the plant was heavily infested with the test organism. The control rating employed for the fungi was a function of the fraction of total leaf which remained unaffected by the test organisms.

A. Powdery Bean Mildew

Tender green bean plants with fully expanded primary leaves were placed adjacent to plants infested with the powdery mildew fungus (ersiphe polygoni) 48 hours prior to the application of the organotin compound. The compound was applied by placing the plants on a revolving turntable and spraying them with a formulation containing the triorganotin compound. Once the spray had dried, the plants were placed in a greenhouse for between 7 and 10 days after which time the amount of mildew on the primary leaves was rated. Untreated plants served as controls. Each of the five compounds tested was employed at a concentration of 100 parts per million (p.p.m.). Two of the compounds were evaluated at a concentration of 20 p.p.m. The control ratings are summarized in the following table.

| Compound | Concentration of Spray(p.p.m.) | Control Rating |
|---|---|---|
| Trineopentyltin Chloride | 100 | 7.3$^P$ |
| Bis(trineopentyltin)Oxide | 100 | 10 |
| Tris(3,3-dimethylbutyl)tin Chloride | 100 | 9.5 |
| | 20 | 9.3 |
| Tris(3,3-dimethylbutyl)tin Hydroxide | 100 | 10 |
| | 20 | 9 |
| Bis(tri-t-butyltin)oxide | 100 | 6.5 |

$^P$=compound exhibited slight phytotoxicity

Only one of the formulations tested was slightly phytotoxic to the bean plants. The others had no observable adverse effects on the plants.

B. Apple Mildew

Apple seeds which had been refrigerated for 60 days were planted in pasteurized soil. When the resultant seedlings were in the fifth leaf stage the plants were sprayed with a formulation containing 10 p.p.m. of trineopentyltin chloride. On the following day they were placed among plants that were heavily infested with apple mildew. The sprayed plants were rated 14–21 days following the initial exposure to the mildew (first rating), after which the plants were again sprayed with the same formulation which had previously been employed. The rating was repeated 20 days following the second spraying. None of the sprayed plants exhibited any phytotoxic effects.

| Concentration (p.p.m) | Control Ratings | |
| --- | --- | --- |
| | First | Second |
| 10 | 8.0 | 5.0 |

C. Apple Scab (Conidia)

Frozen apple leaves which were infested with conidia spores were soaked in cool water for about 30 minutes, following which the liquid phase was filtered through a single layer of cheesecloth. A number of apple seedlings in the fifth leaf stage were sprayed with the water containing the dispersed conidia spores. The seedlings were stored in a high humidity environment [relative humidity (R.H.)=100%] at ambient temperature for two days, after which they were stored at a temperature of 24°±3° C. for seven days, then in the high humidity environment for between one and two days, and finally at 24°±3° C. for 10 to 15 days, during which time the infested leaves were harvested. The leaves were extracted with cool water to prepare a stock solution which when viewed under a microscope at 100× magnification exhibited a field containing not less than 20 canidia spores.

The plants to be tested were sprayed with a liquid formulation containing 250, 50, 12.5 or 3.0 p.p.m. of trineopentyltin chloride. The formulations were prepared as previously described. After the solvent had evaporated the leaves were sprayed with the suspension of conidia spores prepared as described in the preceding paragraph. The plants were then placed in a high humidity (100% relative humidity) environment at ambient temperature for two days, after which they were stored under conditions of ambient humidity and a temperature of 24°±3° C. for 30 days, at which time the plants were rated. The results of the test are summarized below.

| Concentration of Organotin Compound (p.p.m.) | Control Rating |
| --- | --- |
| 250 | 9.0 |
| 50 | 8.0 |
| 12.5 | 7.5 |
| 3.0 | 7.3 |

The untreated control plant exhibited a rating of 3.9.

D. Leaf Spot of Rice (Helminthosporium)

Rice plants were sprayed with formulations containing 200 parts per million of bis(trineopentyltin) oxide, 200 p.p.m. of tris(3,3-dimethylbutyltin) hydroxide or 50 p.p.m. of the latter compound using the procedure described in part A of this section. Once the spray had dried the leaves of the plants were innoculated with a suspension of helminthosporium spores and placed in an incubation chamber (100% relative humidity) for 24 hours, then stored under ambient humidity at a temperature of 24°±3° C. until lesions developed on the leaves of control plants which had not been treated with the organotin compound. The control plants had been innoculated with helminthosporium spores and incubated concurrently with the treated plants. The three treated plants exhibited control ratings of between 7 and 10 when the control plants became completely infested (control rating=0).

D. Tomato Early Blight (Alternaria solani)

Tomato plants of the Bonny Best variety (4–5 weeks old) were placed on a revolving turntable and sprayed with formulations containing 250, 50 or 25 p.p.m. of either tris(3,3-dimethylbutyl)tin chloride or bis(tri-t-butyltin)oxide. Once the liquid had evaporated from the sprayed material the plants were innoculated with a suspension containing spores of the early blight fungus, after which they were placed in an incubation chamber (100% relative humidity) for 24 hours. The plants were then maintained under ambient humidity at a temperature of 24°±3° C. until lesions had developed on the control plants. Each formulation was applied to two plants, and the rating system employed two representative leaves from each of the two plants. The control ratings in the table below represent the average of the four ratings.

| Compound | Conc.(p.p.m.) | Average Effectiveness Rating |
| --- | --- | --- |
| Tris(3,3-dimethylbutyl)tin chloride | 250 | 9 |
| | 50 | 8 |
| | 25 | 8 |
| Bis(tri-t-butyltin)oxide | 250 | 9 |
| | 50 | 9 |
| | 25 | 8 |
| Control(no organotin compound) | — | 5 |

F. Two-spotted Spider Mite

The leaves of bean plants were dipped into a formulation containing a dispersion containing 50 p.p.m. of tris(3,3-dimethylbutyl)tin chloride. A number of adult spider mites were then transferred onto the upper surface of the plant leaves. The plants remained undisturbed at 24°±3° C. for between 8 and 12 days following exposure to the mites, at which time the control rating of 7 was obtained by observing the percentage of dead mites.

None of the spray formulations employed in any of the preceding examples were sufficiently phytotoxic to kill the plants treated with these formulations.

Although the organotin compounds employed to determine biological activity were chlorides, oxides and a hydroxide, other derivatives including fluorides, bromides, carboxylates, mercaptides, alkoxides, phenoxides, carbamates, thiocarbamates, sulfides and sulfates are expected to be at least equally efficacious in combating fungi and mites since it has been shown that the anionic radical of the present triorganotin compounds, represented by X and Y in the foregoing generic formulae, have little, if any, effect of the degree of biological activity exhibited by the compound unless the anion itself possesses significant biological activity.

What is claimed is:

1. A non-phytotoxic composition for combating mites, said composition comprising a liquid or solid carrier and a miticidally effective amount of a compound of the general formula

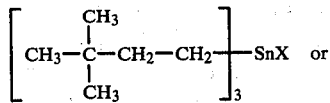 or
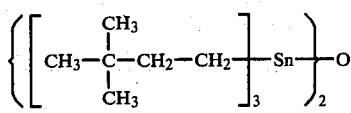
wherein X represents a radical selected from the group consisting of chlorine, bromine, fluorine, hydroxyl and carboxylate
wherein R represents an alkyl radical containing from 1 to 12 carbon atoms.
* * * * *